United States Patent [19]
Musha et al.

[11] Patent Number: 5,797,853
[45] Date of Patent: Aug. 25, 1998

[54] METHOD AND APPARATUS FOR MEASURING BRAIN FUNCTION

[76] Inventors: Toshimitsu Musha, 2-13-17 Minami-tsuhushino, Machida-shi, Tokyo 194; Omi Terasaki, 9-5-1-9-401 Arima, Miyamae-ku, Kawasahi-shi, 216, both of Japan

[21] Appl. No.: 852,672

[22] Filed: May 7, 1997

Related U.S. Application Data

[63] Continuation of Ser. No. 413,503, Mar. 20, 1995, abandoned.

[30] Foreign Application Priority Data

Mar. 31, 1994 [JP] Japan .................... 6-063105

[51] Int. Cl.$^6$ ........................................ A61B 5/05
[52] U.S. Cl. ...................... 600/544; 600/545; 600/546
[58] Field of Search .................... 600/544, 545, 600/546

[56] References Cited

U.S. PATENT DOCUMENTS

| | | | |
|---|---|---|---|
| 4,140,997 | 2/1979 | Brady | 128/732 |
| 4,462,411 | 7/1984 | Rickards | 128/731 |
| 4,524,774 | 6/1985 | Hildebrant . | |
| 4,632,122 | 12/1986 | Johansson et al. | 128/731 |
| 4,651,145 | 3/1987 | Sutter | 128/731 |
| 4,683,892 | 8/1987 | Johansson et al. | 128/731 |
| 4,846,190 | 7/1989 | John | 128/731 |
| 4,926,969 | 5/1990 | Wright et al. | 128/731 |
| 4,974,602 | 12/1990 | Abraham-Fuchs et al. | 128/731 |
| 4,977,896 | 12/1990 | Robinson et al. | 128/731 |
| 4,987,903 | 1/1991 | Keppel et al. | 128/731 |
| 5,003,986 | 4/1991 | Finitzo et al. | 128/731 |
| 5,010,891 | 4/1991 | Chamoun | 128/731 |
| 5,230,346 | 7/1993 | Leuchter et al. | 128/731 |
| 5,243,984 | 9/1993 | Ogura et al. | 128/731 |
| 5,269,315 | 12/1993 | Leuchter et al. | 128/731 |
| 5,293,427 | 3/1994 | Ueno et al. | 382/1 |
| 5,309,923 | 5/1994 | Leuchter et al. | 128/731 |
| 5,360,971 | 11/1994 | Kaufman et al. | 250/221 |

OTHER PUBLICATIONS

D. Flotzinger, et al., "EEG Classification by Learning Vector Quantization", *Biomedizinschne Technik*, 37, pp. 303–309 (1992).

A.S. Gevins, et al., "Effects of Prolonged Mental Work on Functional Brain Topography", *Electroencephalography and Clinical Neurophysiology*, 76, pp. 339–350 (1990).

B. Kemp, "Cerebral Information Processing Estimated by Unpredictability of the EEG", *Clin. Neurol. & Neurosurg.*, 94, pp. S103–S105 (1992).

B. Klöppel, "Neural Networks As A New Method for EEG Analysis", *Neuropsychobiology*, 29, pp. 33–38 (1994).

B. Klöppel, "Application of Neural Networks for EEG Analysis", *Neuropsychobiology*, 29, pp. 39–46 (1994).

(List continued on next page.)

*Primary Examiner*—Jennifer Bahr
*Assistant Examiner*—Stephen Huang
*Attorney, Agent, or Firm*—Fish & Neave; Douglas A. Cardwell

[57] ABSTRACT

An apparatus and method for automatically determining an individual's level of brain function is provided. EEG or MEG signals are collected amplified and digitized. The signals are then passed to a computer comprising a CPU, ROM and RAM, an input interface for collecting and filtering the scalp potential signals and an output interface for displaying the resulting information on a display device such as a printer or CRT. The computer determines the position of these signals in reference to the interpolated 3-D geometry of the subject's head. The dipolarity of a particular point is iteratively and empirically derived by comparing the values of these measured signals to a test signal and the error between the two is minimized. The procedure is repeated for the complete series of electrodes placed on the skull. The mean dipolarity of a subject is then determined for a given time frame. The subject's dipolarity is then compared against that of age matched subjects and scaled so that an estimation of the subjects degree of cognitive loss is determined.

12 Claims, 6 Drawing Sheets

OTHER PUBLICATIONS

S. Roberts, et al., "New Method of Automated Sleep Quantification", *Med. & Biol. Eng & Comput.*, 30, pp. 509–517 (1992).

R.A. Veselis, et al., "Use of Neural Network Analysis to Classify Electroencephalographic Patterns Against Depth of Midazolam Sedation in Intensive Care Unit Patients", *J. Clin. Monit.*, 7, pp. 259–267 (1991).

R.A. Veselis, et al., "Analytical Methods To Differentiate Similar Electroencephalographic Spectra: Neural Network and Discriminant Analysis", *J. Clin. Monit.*, 9, pp. 257–267 (1993).

Nymox Clinical Reference Laboratories, AD7C (trademark) Advertisement, Wall Street Journal (Dec. 1996).

Modern Medicine, "Clinical News" (Sep. 1996).

Nymox Pharmaceutical Corporation Press Release (Oct. 23, 1996).

Nymon Pharmaceutical Corporation Press Release (Aug. 20, 1996).

• DIPOLE # 1
□ DIPOLE # 2

FIG. 3A

• DIPOLE # 1
□ DIPOLE # 2

FIG. 3B

• DIPOLE # 1
□ DIPOLE # 2

METHOD AND APPARATUS FOR MEASURING BRAIN FUNCTION

This is a continuation of U.S. patent application Ser. No. 08/413,503, filed on Mar. 30, 1995, now abandoned.

BACKGROUND OF THE INVENTION

This invention relates to a method and apparatus for automatically measuring the degree of brain function of an individual, and more particularly to quantify the degree of dementia of the human subject to which the apparatus is connected.

Dementia is one of our most pressing public health problems. As the world's population ages, more people enter the age group where they are at risk for disorders that cause dementia. Dementia is generally defined as the acquired and unusual loss of intellectual function. This loss of function encompasses a number of different intellectual capabilities and can be symptomatic of many different disorders, such as Alzheimer's disease, vascular disease, Huntington's disease and Parkinson's disease.

It has been estimated that about 5% of the population over age 65 has severe dementia and about 10% have mild to moderate dementia. Alzheimer type dementia has been observed in as much as 30% of the population over 80. It is believed that the number of persons in the over 65 population group will triple by the year 2050.

The types of loss of cognitive function which are characteristic of the various forms of dementia include defects or lapses in thinking, reduction in language and memory capabilities, and changes in spatial perception ability.

Measurement of a patient's degree of dementia is currently estimated by batteries of neuropsychological tests. These include such tests as the Mini-Mental State (MMS), Mental Status Questionnaire (MSQ), Functional Assessment Staging Test (FAST), Critical Dementia Rating (CDR), the Hasegawa Dementia Scale (HDS), the Nishimura Dementia Scale and the Karasawa Clinical Assessment Scale. These tests inquire about, among other things, the patient's name, dates, familiar locations and test such cognitive abilities as short-term memory and skill learning.

These neuropsychological assessments, although very useful in measuring dementia, suffer from defects in reliability. The assessment is affected by such subjective factors as the moods of the patient and the tester, the relationship between the patient and the tester, and the variations in testing facilities and conditions. Additionally, the repeated administration of a particular test allows for patient learning between administrations. The patient begins to remember the questions and answers, thereby altering the validity of any long-term monitoring study results. What is needed therefore, is a method for measuring brain function which gives results that are both reliable and reproducible.

Historically, overall brain activity has been measured in a number of different ways. Brain function measurement has included such classical methods as the electroencephalogram (EEGs) that measures minute changes in the brain's own electrical activity and its more recent counterpart the magnetoencephalogram (MEGS) that measures the magnetic fields generated by the brain's electrical activity. More exotic methods such as Positron Emission Tomography (PET) scanning which measures the breakdown of radioactive glucose in the brain (and thereby indirectly brain activity) and Magnetic Resonance Imaging (MRI) which produces a "picture" of the brain by "scanning" it with a magnetic field have also gained popularity. All these methods have their limitations and none of them has been able to diagnose and quantify the loss of functioning characteristic of dementia and present in many degenerative brain disorders.

In particular, it has been thought that it was not possible to either measure or even diagnose dementia using conventional electroencephalograms (EEGs). The EEGs of patients with dementia were thought to be predominantly normal with some patients showing varying amounts of slowing. Occasionally, patients showed marked delays in late evoked potentials (P300 waves).

In view of the foregoing, it would be desirable to be able to provide a method and an apparatus for automatically determining an individual's level of brain function, and more particularly to quantify the level of dementia of a human subject to which the apparatus is connected.

SUMMARY OF THE INVENTION

It is an object of this invention to provide a method and apparatus for automatically determining an individual's level of brain function, and more particularly for quantifying the degree of dementia of a human subject to which the apparatus is connected.

Possible applications for such an apparatus and method include, for example: the diagnosis and quantification of brain function loss, such as dementia; the associated early diagnosis of diseases, such as Alzheimer's disease, which evidence such a loss as a symptom; and the more accurate monitoring of the effectiveness of protocols designed to treat diseases which result in various types of brain function loss, including dementia.

These and other objects of the invention are accomplished in accordance with the principles of the invention by providing an apparatus and method for automatically determining an individual's level of brain function. More particularly, this invention provides a system whereby EEG or MEG signals are collected and processed and an individual's degree of dementia is measured. The apparatus comprises a series of sensors, which may include but are not limited to EEG or MEG sensors which measure scalp potentials, an amplifier which amplifies the received signals, a mutliplexer which collects the signals from the various scalp electrodes, and an A/D converter which digitizes the resulting amplified signals.

The system further comprises a digital computer for processing the resulting amplified scalp potential signals. The computer comprises a Central Processing Unit (CPU), Read-Only Memory (ROM), Random Access Memory (RAM), an input interface for collecting and filtering the scalp potential signals and an output interface for displaying the resulting information on a display device such as a printer or CRT.

The apparatus also may include various other input devices such as a digitizer for recording the locations of the scalp sensors, a keyboard for inputing information into the digital computer, and external memory for storing historical data used to scale a particular patient's dipolarity to the patient's degree of cognitive loss.

The invention is accomplished by having a series of sensors detect electrical (EEG) or magnetic (MEG) potentials present on the surface of a subject's head. These signals are then amplified and digitized. The position of these signals is then determined in reference to the interpolated 3-D geometry of the subject's head. The dipolarity of a particular point is iteratively and empirically determined by comparing the values of these measured signals to a test signal and the error between the two is minimized. The procedure is repeated for the complete series of electrodes placed on the skull. The mean dipolarity of a subject is then determined for a given time frame. The subject's dipolarity is then compared against that of age matched subjects and scaled so that an estimation of the subject's degree of cognitive loss is determined.

BRIEF DESCRIPTION OF THE DRAWINGS

The above and other objects and advantages of the invention will be apparent upon consideration of the following detailed description, taken in conjunction with the accompanying drawings, in which the reference numbers refer to like parts throughout and in which.

DETAILED DESCRIPTION OF THE INVENTION

The present invention is an apparatus and method for automatically determining the level of brain functioning of a particular individual. Brain functioning is measured via sensors placed on the scalp of the subject. Most typically, these sensors detect electrical (EEG) or magnetic (MEG) potentials present on the surface of the head. These signals are then amplified and digitized. The position of these signals is then determined in reference to the interpolated 3-D geometry of the subject's head. The dipolarity of a particular point is iteratively determined by comparing the values of these measured signals to test signals and the error between the two is minimized. The procedure is repeated for the complete series of electrodes placed on the skull. The mean dipolarity of a subject is then determined for a given time frame. The subject's dipolarity is then compared against that of age matched subjects and scaled so that an estimation of the subjects degree of cognitive loss is determined.

In particular, this invention measures the "dipolarity" of the brain's electrical or magnetic signals by approximating the brain's electrical activity using equivalent current dipoles. Generally, excitatory activation of a neuron generates electromagnetic currents around the neuron. The distribution of the electric current resembles a current dipole, thus one can model any particular neuron as a small current dipole. When a large number of neurons are excited simultaneously or almost simultaneously, and are located in a particular region of the brain, their electrical activity can be estimated by a single equivalent current dipole. When active neurons are distributed in two separate volumes of the cortex, such as when measuring an individual's α rhythm, their electrical activity can be approximated by two current dipoles. An electrical dipole can be specified using six parameters, three for the coordinates of the dipole (x,y,z) and three for the dipole moment in each direction (px, py, pz). Therefore theoretically one could measure 2 equivalent dipoles using only 12 sensors. Practically, however, a standard array of 21 or 32 sensors can measure only 2 equivalent dipoles, because some redundancy is required to stabilize the dipole estimation against unwanted potential fluctuations.

The goodness of fit of the equivalent current dipole to the actual generated potentials at a particular point is known as the subject's dipolarity ("D"). In particular, this invention operates by minimizing the mean squared deviation between the potentials generated by the equivalent current dipoles and the potentials observed at the corresponding sensor positions.

It is clear that when neuronal activity is located in a small cortical area the dipolarity "D" is close to 100%. It has been empirically determined, for example, that a subject's alpha rhythm can be well approximated using two equivalent dipoles. It has also been found that a normal subject's dipolarity is very close to a 100%. The dipolarity of demented subjects is substantially lower. This lower dipolarity has at least two probable origins. First, when activated neurons are distributed over large cortical areas (as opposed to being highly focused) an individual's dipolarity will be reduced. Second, the random orientation of local neuronal currents will also tend to reduce the subject's dipolarity.

In using this system to estimate an individual's loss of brain function and in particular, an individual's degree of dementia, historical patient data are often useful. One can plot a gradient of dementia having normal subjects at the lowest end of the scale and the most demented subjects at the highest end of the scale. One can then determine the mean dipolarity for both normal and severely demented subjects in a particular age-matched population. An individual's overall dipolarity, a mean of a number of dipolarity measurements, can then be compared to this scale and an estimate of the individual's dementia can be empirically derived.

Figure 1:
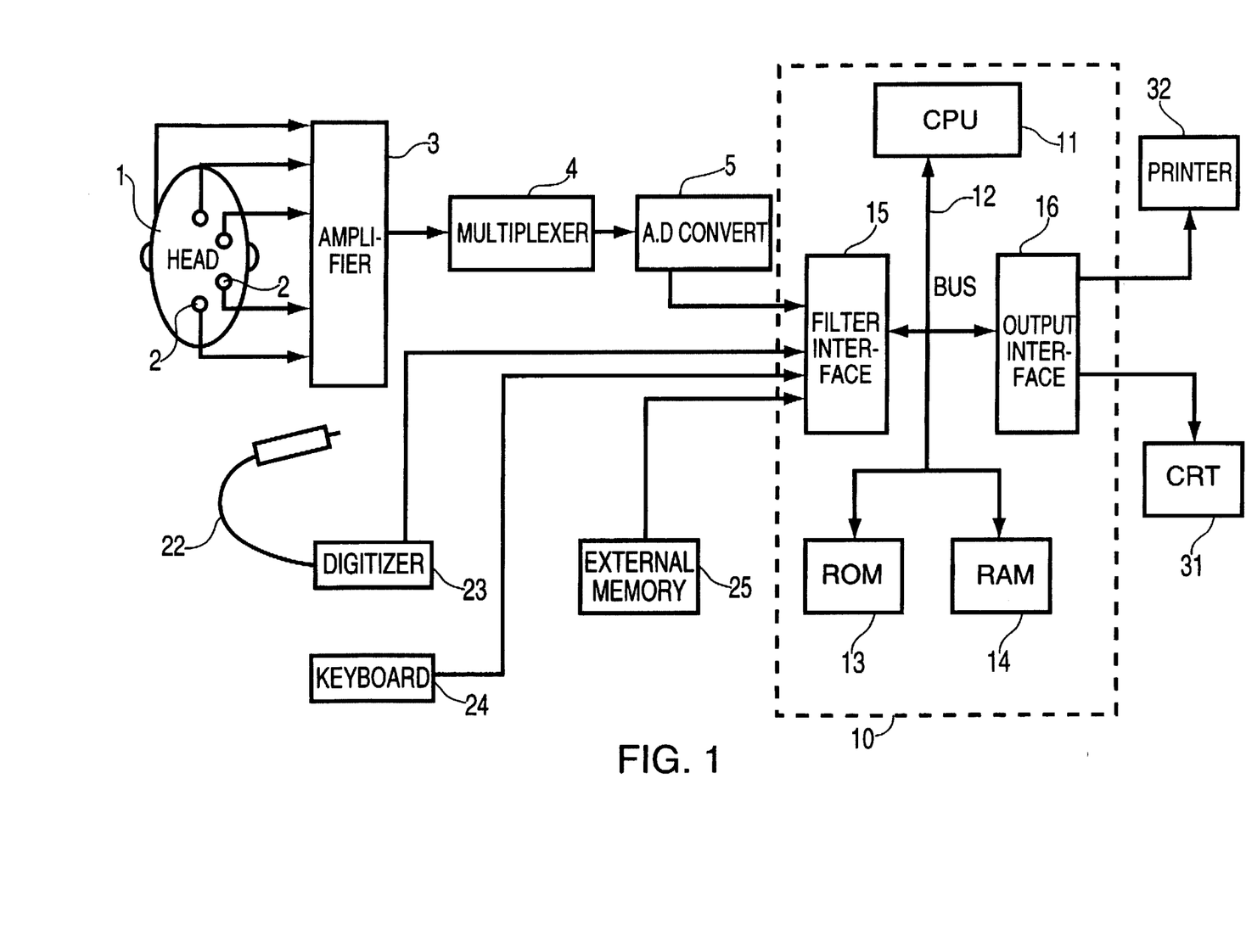
FIG. 1 is a block diagram of a hardware implementation of a preferred embodiment of apparatus for automatically determining the level of brain functioning of the subject.

FIG. 1 is a block diagram of a hardware implementation of a preferred embodiment of the apparatus for automatically determining the level of brain function loss of a subject. A plurality of sensors 2 is placed on a subject's head 1. The plurality of sensors 2 may include but is not limited to EEG and MEG sensors. A plurality of signals 26 from sensors 2 are passed through an amplifier 3 and a multiplexer 4 wherein the signals are amplified and multiplexed. The resulting amplified signals are digitized by an Analog-to-Digital (A/D) converter and are sent to a digital computer 10 by way of a filter interface 15. The filter interface 15 filters out a particular frequency band of signals. EEG signals, for example, are typically divided into several frequency bands. The α band is a band of frequencies ranging from about 8 Hz to about 13 Hz. In addition to the α band there is the δ band (from 1 to about 3 Hz), the θ band (from about 4 to about 7 Hz), the β band (from about 13 Hz to about 30 Hz) and the γ band (above about 30 Hz). The preferred embodiment is drawn to extracting and using the α band, which is usually observed in the occipital region of the head, but the invention can be applied to any of the other bands. Signals other than EEG signals (such as MEG signals) can also be used so that the following description applies.

EEG scalp potentials have been measured using 21 sensors 2 which are arranged according to the International 10-20 standard or alternatively 32 sensors 2 wherein 11 sensors 2 have been added to the 21 sensors 2 arrangement. In particular a subject's α rhythms have been analyzed and used to estimate the subject's dipolarity. Alpha rhythms are usually observed in individuals when their eyes are closed. These rhythms can appear either continuously or intermittently as a wave-packet or a spindle. Because α rhythms are present in both the right and left hemispheres of the occipital region they are better approximated by a pair of current dipoles.

In addition to signals from sensors 2 the computer 10 will take into account information concerning the shape of the subject's head and the position of the sensors 2. This information is either available as information stored internally in the computer's RAM 14 or is provided by an external position sensor 22 through a digitizer 23 and a the filter interface 15. A keyboard 24 may also be used to provide patient data to the computer 10 through the filter interface 15. In addition to the filter interface 15 the computer comprises a CPU 11 for processing information, calculating the subject's dipolarity, and determining the subject's degree of brain function loss. Read-Only memory (ROM) 13 which stores software for calculating the equivalent dipoles. Random-access memory (RAM) 14 for storing patient head information, and storing information received from the keyboard 24 and the A/D converter 5 via the filter interface 15 and an output interface 16 which sends information such as the degree of dementia to external devices such as a CRT 31 or a printer 32. The CPU 11, the filter interface 15, the output interface 16, the ROM 13 and the RAM 14 are all connected by way of a bus 12.

Figure 2A:
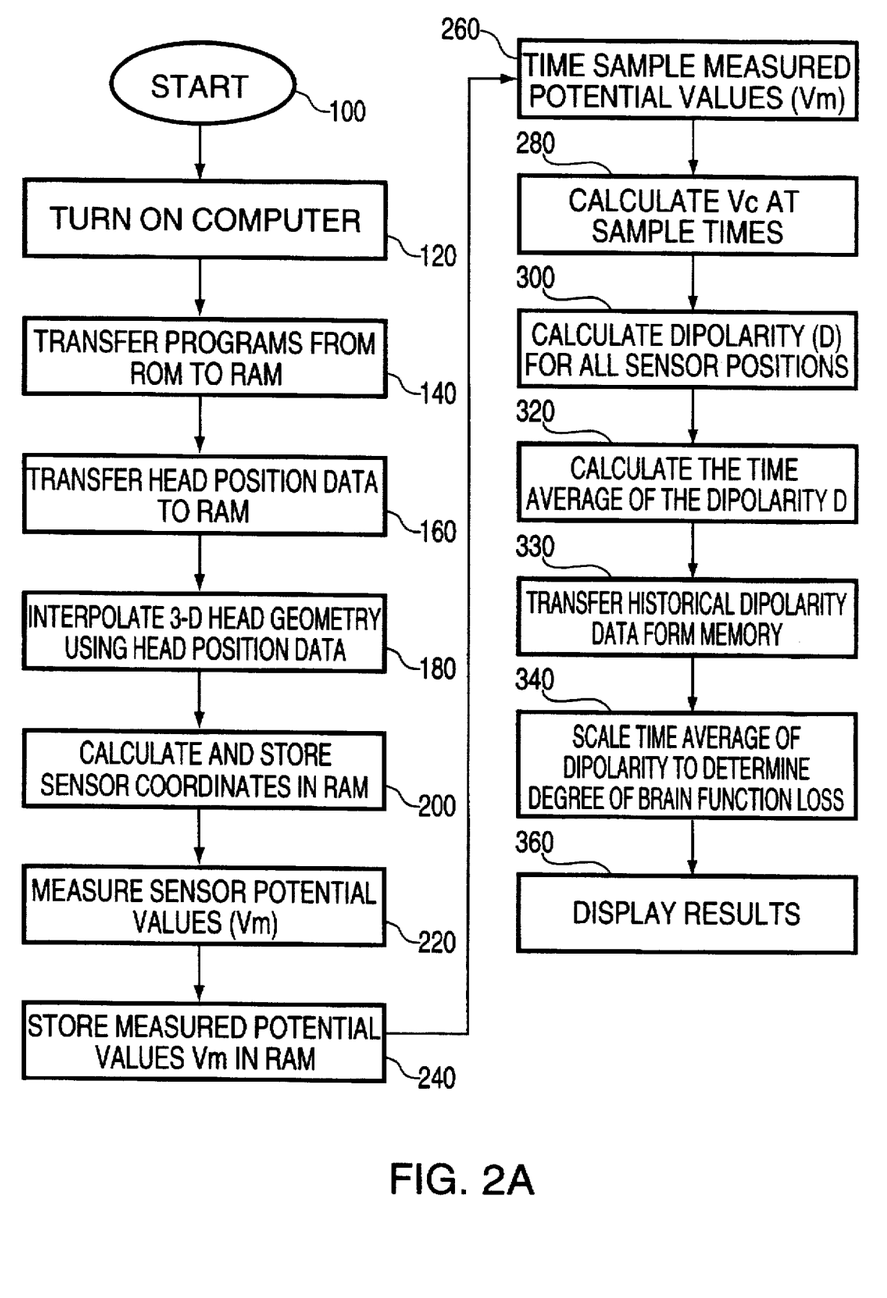
FIGS. 2a and 2b are flowcharts showing the steps involved in automatically determining the level of brain functioning of the subject.

FIG. 2a shows the steps involved in the process 100 of automatically determining the brain function loss of an individual. In step 120 the computer 10 is turned on. Programs for determining the head geometry, processing the EEG signals received from the sensors 2, and determining the subject's dipolarity are loaded from ROM 13 in step 140. Head position data, including the size of the head and the position of the sensors 2, may be loaded into RAM 14 from the digitizer 23 at step 160. Alternatively, the information as to head size may already be present in RAM 14. The three dimensional geometry of the head is then interpolated at step 180 using the head position data. It is well known in the art to interpolate a three dimensional object using data points on the surface of the object. Once the three dimensional geometry of the head is determined the coordinates of the sensors can be calculated relative to the head geometry and stored in RAM 14 at step 200. In a particular embodiment of this invention, sensors 2 are pre-positioned on a cap, thereby establishing their relative positions and rendering both step 200 and the digitizer 23 unnecessary. Sensor 2 potential values (Vm) are then measured at each of the sensors 2 on the head 1. The resulting values are stored in RAM at step 240. Vm is then sampled periodically (typically every 1 ms for 10 msec) at step 260.

At step 280 potential values Vc for each sensor 1 are calculated for the sample times in step 260 based on the generation of 2 theoretical equivalent dipoles. The subject's dipolarity D is calculated at step 300 based on either of the following formulas:

$$D = \sqrt{1 - \frac{av(Vc - Vm)^2}{av(Vm)^2}}$$

or $$D = \sqrt{1 - \frac{(av(Vc - Vco)(Vm - Vmo))^2}{av(Vc - Vco)^2 av(Vm - Vmo)^2}}$$

where Vm and Vc have already been defined. Vco and Vmo are the mean values of Vc and Vm over all the sensor positions and av means "the average of."

The subject's dipolarity D is then averaged over a period of time at step 320. Historical dipolarity data is then transferred from external memory 25 at step 330 and is used at step 340 to scale the particular subject's dipolarity to the related loss of brain function on the age of the subject.

The results including the subject's dipolarity and a scaled score indicating degree of loss of brain function are then displayed at step 360 on a CRT 31 or printed on a printer 32.

Figure 2B:
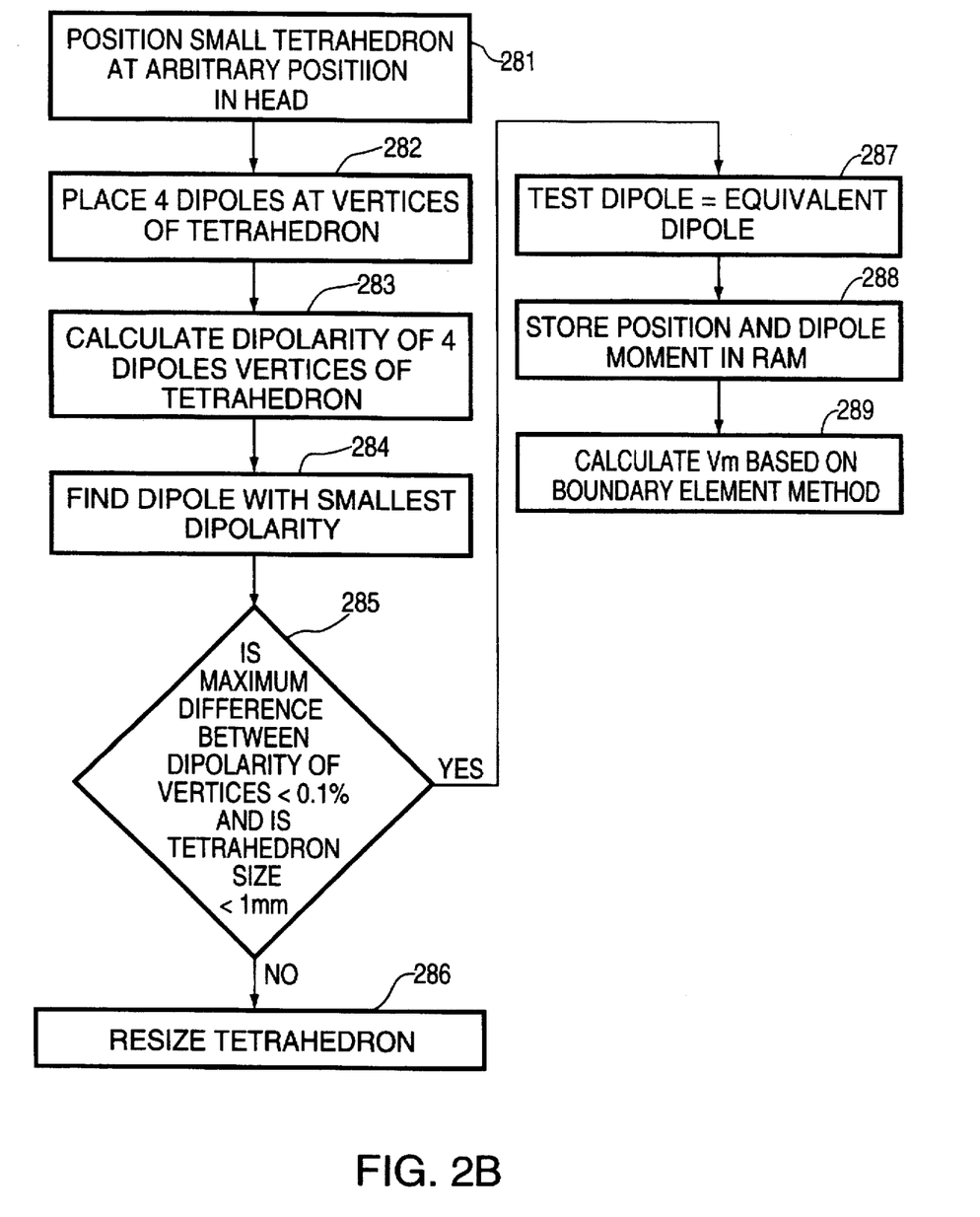

FIG. 2b describes how Vc is calculated. At step 281 a small tetrahedron is positioned in an arbitrary position in the head near a particular sensor. Four current dipoles are placed at the vertices of the tetrahedron at step 282. Next at step 283 the dipolarity of the four dipoles at the vertices of the tetrahedron are calculated. The dipole with the smallest dipolarity is then determined at step 284. It is then determined at step 285 whether (1) the largest difference between the dipolarities of the four vertices is less than 0.1% of the mean dipolarity of the four vertices; and (2) whether the tetrahedron size is less than 1 mm. If both conditions are satisfied then the test dipole is found to be the equivalent dipole at step 287. The position and dipole moment of the equivalent dipole are then stored in RAM 14 at step 288 and Vc is calculated at step 289 based on the boundary element method which is well known in the art. If the conditions of step 285 fail to be satisfied the tetrahedron undergoes a point reflection at step 286 through the point belonging to the dipole with the smallest dipolarity. At this time the tetrahedron is resized, shrinking as the minimum difference of the four dipolarities decreases. Steps 283 to 285 are then repeated.

Figure 3A:
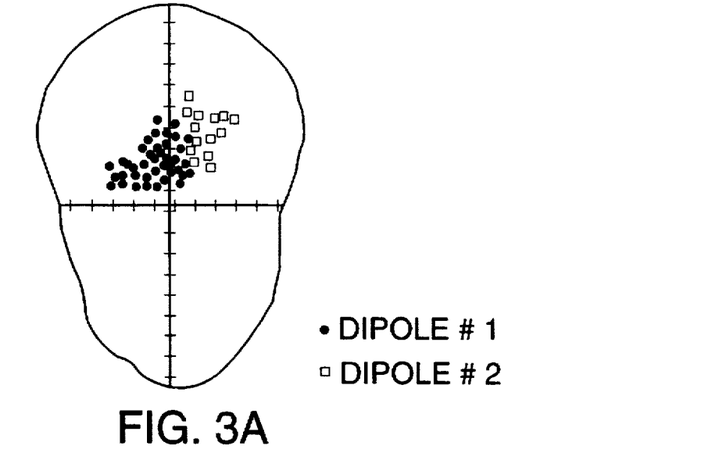
FIGS. 3a-3c show frontal, axial and sagittal views, respectively, of equivalent dipole pairs of a normal human subject.
Figure 3B:
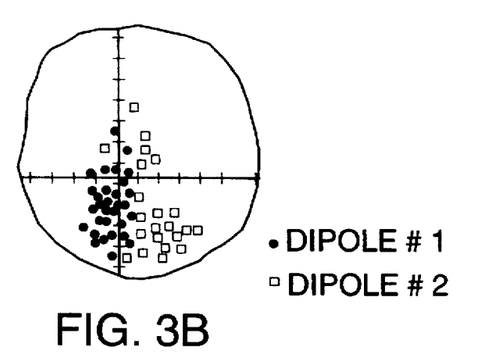
Figure 3C:
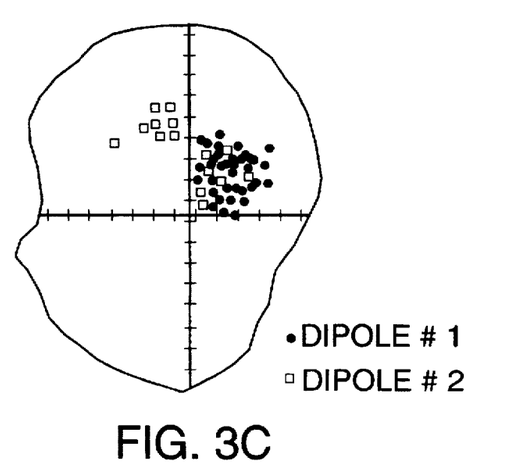

FIGS. 3a-3c show the result of the above method on a normal subject. The figures are a graphical representation of the spatial orientation of the calculated equivalent dipoles in a normal subject. In particular, they show frontal, axial and sagittal views of the equivalent dipoles found for a normal subject pursuant to the invention.

Figure 4:
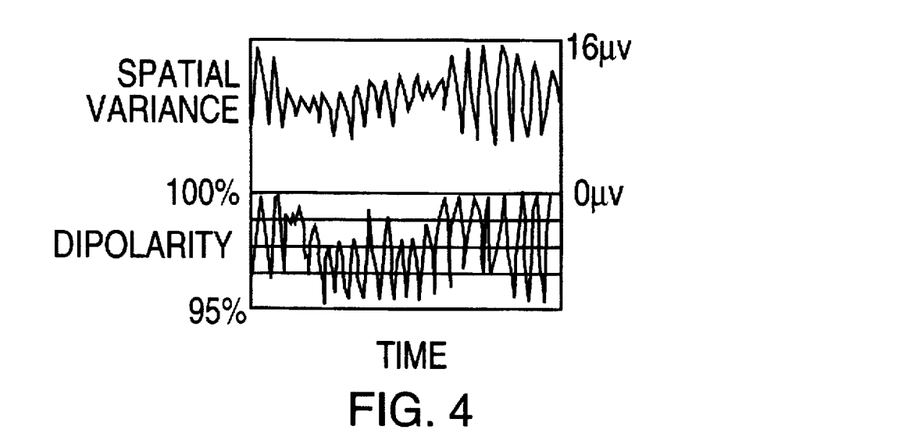
FIG. 4 shows the spatial variance of the mean squared potentials and the dipolarity of a normal human subject's alpha rhythm.

FIG. 4 shows the spatial variance of the mean squared potentials and the dipolarity of a normal subject's alpha rhythms. As one can see, the spatial variance is as high as 16 μV and has substantial variability and the mean dipolarity over time is fairly high and usually over 98%.

Figure 5A:
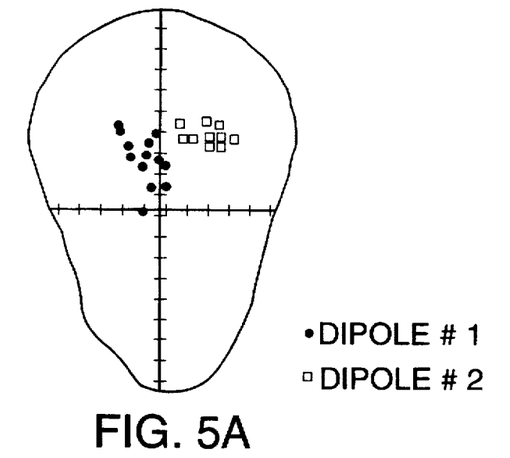
FIGS. 5a-5c show frontal, axial and sagittal views, respectively, of equivalent dipole pairs for a demented subject.
Figure 5B:
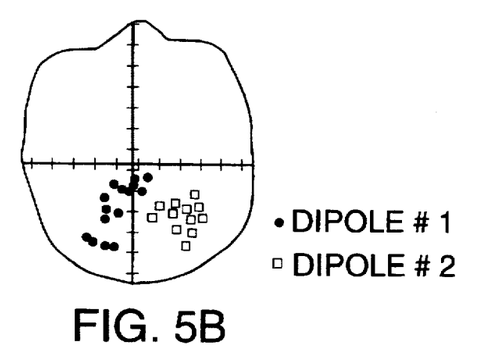
Figure 5C:
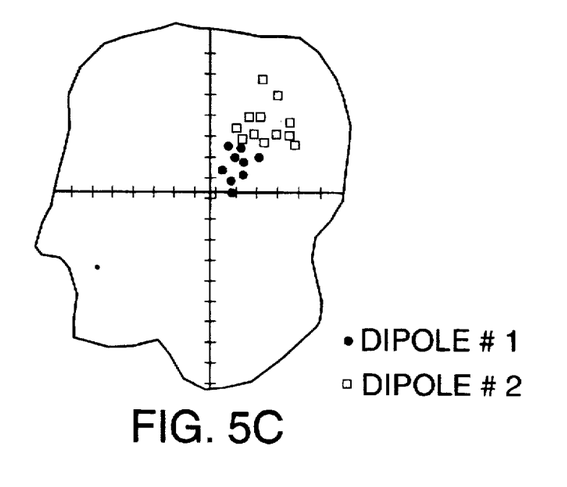

FIGS. 5a-5c show, respectively, frontal axial and sagittal views of the locations of equivalent dipole pairs for a demented subject. It is obvious from the figures that far fewer equivalent dipole pairs can be generated in the instance of a severely demented patient.

Figure 6:
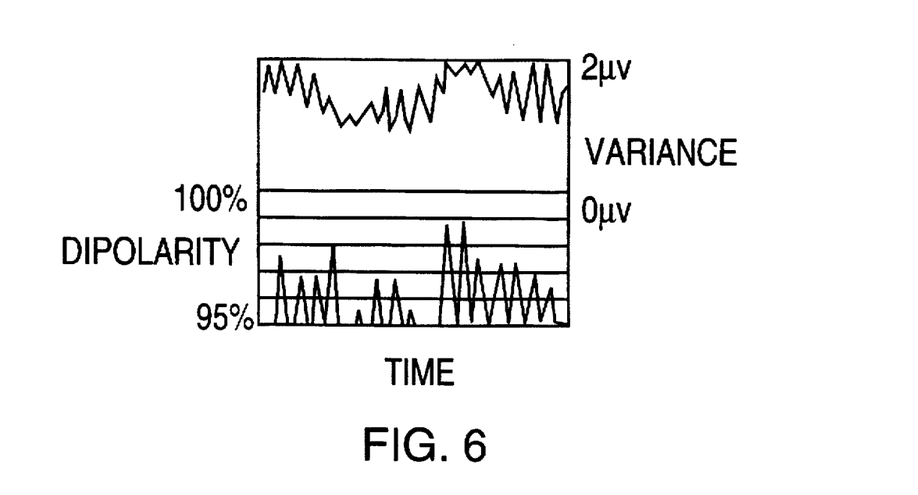
FIG. 6 shows the spatial variance of the mean squared potentials and the dipolarity of a demented subject's alpha rhythm.

FIG. 6 shows the spatial variance of the mean squared potentials and the dipolarity of a demented subject's alpha rhythms. As one can see, the average spatial variance is lower and has less variability than a normal subject and the mean dipolarity over time is relatively low barely rising above 95%.

Thus it can be seen that a method and an apparatus for automatically determining the level of brain function of an individual, and more particularly measuring the degree of dementia of a human subject, is provided. One skilled in the art will appreciate that the present invention can be practiced by other than the described embodiments, which are presented for purposes of illustration and not of limitation, and the present invention is limited only by the claims which follow.

What is claimed is:

1. For use with a human subject having a head and having a level of brain function susceptible to loss, an apparatus for automatically determining the level of brain function loss of the human subject said apparatus comprising:
   - a plurality of sensors which produce output signals for detecting electromagnetic signals of the human subject when applied to said head of the human subject corresponding to a particular range of electromagnetic frequencies;
   - an amplifier for amplifying said output signals;
   - means for digitizing said output signals;
   - a computer comprising:
     - a filter for filtering said output signals,
     - a processor for determining the human subject dipolarity, wherein the human subject dipolarity is a mean dipolarity determined for a given time frame,
     - output interface means for displaying the human subject dipolarity,
     - read-only memory, and
     - random access memory;
   - analyzing means for analyzing the human subject dipolarity and determining the human subject level of brain function loss; and
   - a display for displaying the level of brain function loss of the human subject.

2. The apparatus of claim 1 wherein said plurality of sensors detects EEG potentials at a plurality of points on scalp of the subject.

3. The apparatus of claim 1 wherein said plurality of sensors detects MEG potentials at a plurality of points on scalp of the subject.

4. The apparatus of claim 1 or claim 2 wherein said range of electromagnetic frequencies is α band.

5. The apparatus of claim 1 or claim 2 wherein said range of electromagnetic frequencies is βband.

6. The apparatus of claim 1 or claim 2 wherein said range of electromagnetic frequencies is γ band.

7. For use with a human subject having a head and having a level of brain function susceptible to loss, a method for automatically determining the level of loss of brain function of the human subject, said method comprising the steps of:

detecting electromagnetic signals from said head of the human subject and producing output signals corresponding to a particular range of electromagnetic frequencies;

amplifying said output signals;

digitizing said output signals;

comparing said output signals to a series of calculated potentials to determine the human subject dipolarity, wherein subject dipolarity is a mean dipolarity determined for a given time frame;

analyzing the human subject's dipolarity to determine the level of brain function loss; and displaying the level of loss of brain function of the human subject.

8. The method of claim 7 wherein said step of detecting characteristic values comprises detecting EEG potentials at a plurality of points on scalp of the subject.

9. The method of claim 7 wherein said step of detecting characteristic values comprises detecting MEG potentials at a plurality of points on scalp of the subject.

10. The method of claim 8 or claim 9 wherein said range of electromagnetic frequencies is β band.

11. The method of claim 8 or claim 9 wherein said range of electromagnetic frequencies is β band.

12. The method of claim 8 or claim 9 wherein said range of electromagnetic frequencies is γ band.

* * * * *